(12) United States Patent
Albert et al.

(10) Patent No.: US 8,003,616 B2
(45) Date of Patent: Aug. 23, 2011

(54) COMPOSITION FOR THE TREATMENT OF EAR INFECTIONS AND METHOD

(76) Inventors: Rory J. Albert, Scottsdale, AZ (US); Michael R. Blaire, Scottsdale, AZ (US)

( * ) Notice: Subject to any disclaimer, the term of this patent is extended or adjusted under 35 U.S.C. 154(b) by 1397 days.

(21) Appl. No.: 10/830,548

(22) Filed: Apr. 23, 2004

(65) Prior Publication Data

US 2005/0239722 A1 Oct. 27, 2005

(51) Int. Cl.
*A01N 43/04* (2006.01)
*A61K 31/70* (2006.01)
*A61F 9/02* (2006.01)

(52) U.S. Cl. .......................................... 514/28; 424/437
(58) Field of Classification Search ...................... 514/28
See application file for complete search history.

(56) References Cited

U.S. PATENT DOCUMENTS
5,753,269 A 5/1998 Groh et al. .................... 424/618

FOREIGN PATENT DOCUMENTS
EP 0179583 A1 * 4/1986

OTHER PUBLICATIONS
Ansel, H.C. Introduction to Pharmaceutical Dosage Forms, 1985, 4th Edition, Lea &Febiger, pp. 337-341.*
Troy, D.B., Ed. Remington: The Science and Practice of Pharmacy, 2006. 21st Edition, Lippincott Williams & Wilkins, pp. 1080-1082.*
Freedom of Information Summary, ANADA 200-287, GBC Ointment, Phoenix Scientific, Inc., Mar. 28, 2003.
Freedom of Information Summary, NADA 141-177, MOMETAMAX Otic Suspension for Dogs, Schering-Plough Animal Health, Publication date not known, but published prior to Apr. 2003.
"Medical Treatment of Otitis Externa," Stephen White, Publication date not known, but published before Apr. 2003.
Lecture Notes, Jan. 2003 Dermatology, Daniel O. Morris, D.V.M., District of Columbia Academy of Veterinary Medicine, "Otitis Externa and Media: Diagnosis and management in the age of antibiotic resistance," Jan. 2003.
Freedon of Information Summary, NADA 140-810, Feb. 3, 1989, Biomed Laboratories, Panavet Ointment.
Product labeling for Otomax® Otic Antibiotic-Steroid, NADA 140-896, Schering-Plough, Publication date not known, but published before Apr. 2003.
Baytril® Otic, product information by Bayer Health Care, Animal Health Division, original publication date not known, but published prior to Apr. 2003.
Jan. 2001 Press Release for Baytril® Otic, dated Jan. 2001.
Baytril® Otic product labeling, Bayer Health Care LLC, Animal Health Divison, publication date not known, but originally published prior to Apr. 2003.

* cited by examiner

*Primary Examiner* — Sreeni Padmanabhan
*Assistant Examiner* — Samira Jean-Louis
(74) *Attorney, Agent, or Firm* — Cahill Glazer PLC

(57) ABSTRACT

A composition for treating ear infections in animals includes an antifungal agent, an antibiotic agent, a steroidal anti-inflammatory agent, and an acid dissolved to form a liquid. The acid aids in keeping the steroidal anti-inflammatory agent in solution, and enhances the bactericidal effect of the composition. The method of preparing such composition includes dissolving the antifungal agent, steroidal anti-inflammatory agent, and acid in dehydrated alcohol, dissolving the antibiotic agent in propylene glycol, combining the two solutions together, heating the combination and then cooling the composition. Several drops of the composition are applied at least twice per day to the affected area of the animal's ear.

5 Claims, No Drawings

COMPOSITION FOR THE TREATMENT OF EAR INFECTIONS AND METHOD

BACKGROUND OF THE INVENTION

1. Field of the Invention

The present invention relates generally to compositions for the treatment of ear infections in animals, and more particularly, to an improved composition of such type, as well as a method for manufacturing such improved composition.

2. Description of the Related Art

Ear infections, including bacterial infections such as otitis media/externa, fungal infections, and yeast infections, are common among animals, especially canines. Various compositions for treating ear infections in animals are available on the market. One such prior art composition includes ketoconazole, ofloxacin, and triamcinolone diacetate, as active ingredients, along with dehydrated alcohol and propylene glycol as solvents. However, this composition has a cloudy consistency, and requires vigorous shaking prior to use. Among the drawbacks of using such a non-homogeneous solution are the need to repeatedly shake such composition, and the lack of consistency in applied dosage of such composition with each use.

Other compositions for treating ear infections in animals are known wherein acetic acid is included as a mild antibacterial agent. However, those skilled in the art have been discouraged from attempting to combine acetic acid with commonly-used steroidal anti-inflammatory agents (such as triamcinolone diacetate, betamethesone, hydrocortisone, and dexamethasone) because acetic acid tends to drive these steroidal agents out of solution when ordinary methods of preparing such compositions are employed.

Accordingly, it is an object of the present invention to provide an improved composition effective for treating a variety of ear infections in animals, including bacterial infections, fungal infections, and yeast infections.

Another object of the present invention is to provide such a composition wherein the components thereof are more reliably maintained in solution.

Yet another object of the present invention is to provide such a composition which need not be shaken so vigorously before each use.

A further object of the present invention is to provide such a composition which can be administered in more consistent dosages.

A still further object of the present invention is to provide such a composition which enhances the bactericidal effect of the steroidal anti-inflammatory agent by maintaining such agent in solution.

These and other objects of the present invention will become more apparent to those skilled in the art as the description of the present invention proceeds.

SUMMARY OF THE INVENTION

Briefly described, and in accordance with the preferred embodiments thereof, the present invention relates to a liquid composition which is effective in the topical treatment of animal ear infections, its method of formulation, and its manner of use to treat ear infections in animals. The composition includes an antifungal agent, an antibiotic agent, a steroidal anti-inflammatory agent, and an acid. In the preferred embodiment, the composition further includes dehydrated alcohol and propylene glycol to dissolve and combine the previously-mentioned components.

The antifungal agent of the composition is preferably selected from the group of topical antifungal agents consisting of polyenes, azoles, allylamines, morpholines, antimetabolites, and combinations thereof. More specifically, the antifungal agent is ideally selected from the group of antifungal agents consisting of amphotericin, nystatin, fluconazole, itraconazole, clotrimazole, ketoconazole, terbinafine, 5-fluorocytosine, and combinations thereof. The antifungal agent is preferably provided in a concentration of approximately 5 to 50 grams per liter of the composition.

The antibiotic agent used to formulate the aforementioned composition is preferably selected from the group consisting of ofloxacin, ciprofloxacin, neomycin, polymixin B, enrofloxacin, marbofloxacin, orbofloxacin, and combinations thereof. Ideally, the antibiotic agent is provided in a concentration of approximately 0.5 to 5 grams per liter of the composition.

The steroidal anti-inflammatory agent used to formulate the above-described composition is preferably selected from the group consisting of triamcinolone, betamethesone, hydrocortisone, dexamethasone, and combinations thereof. In the preferred embodiment, the steroidal anti-inflammatory agent is provided in a concentration of approximately 0.25 to 2.5 grams per liter of the composition.

The acid used in formulating the aforementioned composition is preferably selected from the group of acids consisting of citric acid, ascorbic acid, glycolic acid, tartaric acid, and combinations thereof. Ideally, this acid is an anhydrous acid to avoid the addition of water to the composition. In the preferred embodiment of the present invention, the anhydrous acid is provided in a concentration of at least approximately 3 grams per liter of the composition.

A preferred form of such composition includes ketoconazole as the antifungal agent, ofloxacin as the antibiotic agent, triamcinolone diacetate as the steroidal anti-inflammatory agent, and citric acid.

Formulation methods are practiced to ensure that the resulting composition is homogeneous. In this regard, the preferred formulation method dissolves the antifungal agent, the steroidal anti-inflammatory agent, and the anhydrous acid in liquid dehydrated alcohol to form a first solution. The antibiotic agent is separately dissolved in liquid propylene glycol to form a second solution. The first and second solutions are then combined to form a third solution; this third solution is then heated. Ideally, the container used to heat the third solution is covered, as by an impervious plastic film, and the third solution is preferably stirred during heating. It is theorized that the step of covering the container during prevents the dehydrated alcohol from evaporating and helps keep the steroidal anti-inflammatory agent in solution for a more homogenous solution. The solution is then cooled back to room temperature, preferably with continued stirring during the cool down phase.

The present invention also relates to the method of treating ear infections in animals by formulating a composition of the type described above, and applying such composition inside the ear of the animal at least twice per day until the ear infection has been cured.

DETAILED DESCRIPTION OF THE PREFERRED EMBODIMENT

A composition for the topical treatment of ear infections in animals, formulated in accordance with the preferred embodiment of the present invention, includes each of the following active ingredients: an antifungal agent, an antibiotic agent, a steroidal anti-inflammatory agent, and an anhydrous acid. The preferred composition also includes dehydrated alcohol and propylene glycol as solvents for maintaining the forgoing active ingredients in solution.

An antifungal agent is generally defined as a drug that selectively eliminates fungal pathogens from a host with minimal toxicity to the host. Some antifungal agents are selective in the types of fungal infections which they attack, while other antifungal agents are effective to treat a broad spectrum of fungal infections. The composition of the present invention preferably utilizes a topical antifungal agent of the latter type, having the ability to topically treat fungal infections caused by organisms such as *Malassezia, Candida, Trichophyton,* and *Microsporum.* Among the major groups of antifungal agents having applicability to the present invention are the polyenes, the azoles, the allylamines, the morpholines, and antimetabolites, as well as combination of one or more of such antifungal agents. While broad spectrum antifungal agents are preferred, the inventors further contemplate that selective antifungal agents may also be used, if desired.

The following are representative antifungal agents within each of the general groups of antifungal agents mentioned above: (a) Polyenes: amphotericin and nystatin; (b) Azoles: fluconazole, itraconazole, clotrimazole, and ketoconazole: (c) Allylamines: terbinafine; and (d) Antimetabolites: 5-fluorocytosine. As mentioned above, combinations of such antifungal agents may also be used, if desired. Other suitable antifungal agents which may be used in practicing the present invention may be found in "Drug Facts and Comparisons, 2002," published by Facts And Comparisons.

When preparing the composition, the antifungal agent is preferably provided in powder form and is dissolved in dehydrated alcohol. Pre-formed tablets of such antifungal agent may be crushed to obtain such powder form. However, it is preferable to begin with an antifungal agent in pure powdered form, since fillers present in some tablets may result in a cloudy, non-homogeneous solution. The concentration of the antifungal agent used in preparation of the composition may range between approximately 5 and 50 grams per liter, and more preferably, approximately 20 grams per liter.

An antibiotic or antibacterial agent is generally defined as a drug that selectively eliminates bacteria from a host with minimal toxicity to the host. As with the antifungal agent, the antibiotic agent is preferably a broad spectrum type antibiotic effective in killing a wide range of bacteria; if desired, a selective-type antibiotic may also be used. Suitable antibiotic agents include, but are not limited to, ofloxacin, ciprofloxacin, neomycin, polymixin B, enrofloxacin, marbofloxacin, orbofloxacin, as well as combinations of such agents. Other suitable antibiotic agents which may be used in practicing the present invention may be found in "Drug Facts and Comparisons, 2002," published by Facts And Comparisons.

It is again preferred that the antibiotic agent be provided in powdered form at the time that the composition is formulated. The antibiotic agent powder is dissolved in liquid propylene glycol. Pre-formed tablets of such antibiotic agent may be crushed to obtain such powder form. However, it is again preferable to begin with an antibiotic agent in pure powdered form, since fillers present in some tablets may not fully dissolve. The concentration of the antibiotic agent used in preparation of the composition may range between approximately 0.5 and 5 grams per liter, and more preferably, approximately 3 grams per liter.

Suitable steroidal anti-inflammatory agents, also known as adrenocortical steroids, for use with the composition of the present invention include triamcinolone, betamethesone, hydrocortisone, dexamethasone, and combinations thereof. Other suitable steroidal anti-inflammatory agents which may be used in practicing the present invention may be found in "Drug Facts and Comparisons, 2002," published by Facts And Comparisons.

When preparing the composition, as in the case of the antifungal agent mentioned above, the steroidal anti-inflammatory agent is preferably provided in powder form and is dissolved in dehydrated alcohol. Once again, pre-formed tablets of such steroidal anti-inflammatory agent may be crushed to form a powder, but it is preferable to begin with a steroidal anti-inflammatory agent in pure powdered form. The concentration of the steroidal anti-inflammatory agent used in preparation of the composition may range between approximately 0.25 and 2.5 grams per liter, and more preferably, approximately 1 gram per liter.

An anhydrous organic acid, or anhydride, is generally defined as a water-free molecule that has a pH lower than 7.0. Various anhydrous organic acids which can be used in formulating the composition of the present invention include the anhydrous forms of citric acid, ascorbic acid, glycolic acid, and tartaric acid (and combinations thereof) all of which may be dissolved in dehydrated alcohol. When preparing a composition in accordance with the present invention, the anhydrous organic acid is preferably provided in powdered form and is dissolved in dehydrated alcohol. The concentration of acid used in preparation of the composition should be approximately at least 3 grams per liter of composition, and more preferably, approximately 5 grams per liter of composition.

The presence of the organic anhydrous acid in the composition of the present invention is believed to provide a beneficial, unexpected effect of increasing the antibacterial effectiveness of the compound. Additionally, it has been found that inclusion of the anhydrous acid also helps to keep the steroidal anti-inflammatory agent fully-dissolved in solution, whereas hydrous acids, such as acetic acid, tend to exhibit the opposite effect. Accordingly, the composition of the present invention need not be agitated or shaken to a significant extent, if at all, after packaging, and dispensed dosages tend to be more uniform.

As noted above, the solvent used to dissolve the antifungal agent, steroidal anti-inflammatory agent, and anhydrous acid, is preferably a liquid dehydrated alcohol, e.g., dehydrated ethanol. It is preferable to use a minimal amount of such dehydrated alcohol, i.e., just enough to dissolve the antifungal agent, steroidal anti-inflammatory agent, and anhydrous acid.

The solvent used for dissolving the antibiotic powder is preferably liquid propylene glycol. In preparing the solution, a sufficient amount of propylene glycol is added to bring the solution to the desired final concentration.

After combining the dehydrated alcohol solution (containing the dissolved antifungal agent, steroidal anti-inflammatory agent, and anhydrous acid) and the propylene glycol solution (containing the dissolved antibiotic agent), the composition is continuously stirred and heated, generally at least until the solution becomes clear and homogenous. The solution is then cooled to room temperature, while continuously stirring. An impervious plastic film (similar to common food wrapping plastic film) or other seal is used to cover the open end of the container used to hold the solution during the heating and cooling processes, and the solution is preferably kept sealed or covered thereafter, for a longer shelf life. It is believed that use of a seal, especially during the heating process, prevents the dehydrated alcohol from evaporating, and results in a homogenous mixture which does not have to be stirred or shaken-up prior to use. Also, it is best to prepare the composition in a low-humidity environment to avoid the introduction of water into the composition during formulation.

The following are examples of the method of preparing preparation a composition in accordance with the present invention.

EXAMPLE 1

Step 1) Approximately 20 grams of the antifungal agent ketoconazole powder (also known by the brand name "Nizoral®" available from Janssen Pharmaceutica Products, LP of Titusville, N.J.), 1 gram of the steroidal anti-inflammatory agent triamcinolone diacetate powder (also known by the brand name Aristocort®), and 5 grams of citric acid powder are dissolved in approximately 50 ml. of dehydrated liquid ethanol alcohol to form a first solution. All of such components are commercially available from Spectrum Pharmacy Products, 7400 N. Oracle Road, Suite 228, Tucson, Ariz. 85704. While triamcinolone diacetate is a preferred steroidal anti-inflammatory, triamcinolone acetonide may also be used. Those skilled in the art will recognize that triamcinolone acetonide is another salt form of triamcinolone.

Step 2) Approximately 3 grams of the antibiotic agent ofloxacin powder (also known by the brand names "Floxin" and "Ocuflox"), available from the R. W. Johnson Pharmaceutical Research Institute of Raritan, N.J., is dissolved in approximately 100 ml. of propylene glycol liquid to form a second solution.

Step 3) The first and second solutions formed in Steps 1 and 2, respectively, are combined within the container of a heating/agitation unit to form a third solution, and propylene glycol liquid is added to bring the total third solution volume to 1 liter. For example, a heating/agitation unit of the type known as the "Thermolyne Cimarec III™" brand hot plate, available from Barnstead Thermolyne Corp. International of Dubuque, Iowa, may be used for such purpose. This type of hot plate includes a magnetic stirrer inside the solution container. The Thermolyne Cimarec III™ brand hot plate is adjusted to a heat setting of "7", and to an agitation setting of "5." The solution container is also covered with the impervious plastic film prior to heating, preferably, as soon as all the components are added thereto.

Step 4) The solution of step 3 is heated, while being continuously stirred, until it turns from a cloudy yellow to a clear reddish purple color, at which point the source of heat is turned off. At this point, the solution may appear to be steaming. This heating process takes a little over two hours; during such heating process, the solution changes color from yellow to orange, from orange to red, and finally to a reddish purple color at the end of approximately two hours.

Step 5) The solution is left on the hot plate and allowed to cool to room temperature while continuing to be stirred during the cool-down phase. Cooling time is approximately three hours.

EXAMPLE 2

The same procedure is followed as set forth in Example 1 above, except that 3 grams of the antibiotic agent ciprofloxacin is used instead of the ofloxacin mentioned in Example 1 above. Ciprofloxacin is available from Bayer Corporation Pharmaceutical Division, of West Haven, Conn.

The compositions formed in the above examples result in non-cloudy, homogeneous solutions, which do not have to be stirred, or shaken-up, prior to use. Dosage and period of use of the composition may vary from approximately 1 to 10 or more drops (note: 1 cm$^3$ of composition corresponds to approximately 20 drops) in each ear, at least once, and preferably, twice daily, for several days to several weeks, depending on the severity of the infection. The preferred dosages are approximately 3 to 4 drops, twice daily, for smaller dogs; 6 to 7 drops, twice daily, for medium-sized dogs; and 9 to 10 drops, twice daily, for large dogs. If desired, the infected ear may be cleansed or flushed prior to administration of the composition.

The composition of Example 1 was used on dogs having ear infections of varying degrees of severity, and was administered into the affected ear(s) according to the following tapering dose schedule: ½ dropperful doses of such composition twice daily for the first week; ½ dropperful doses once daily for the second week; then ½ dropperful doses every other day for a total of four more doses. In dogs having particularly severe infections, infected ears were first flushed with ear flushes containing 2% acetic/2% boric acid before treating with the composition of Example 1. The above protocol was repeated as necessary when symptoms of ear infection reoccurred. Use of the composition proved to be very successful, especially for dogs having chronic, recurring ear infections. It was found that the duration between bouts of ear infections increased due to use of the present composition, and that the need for the use of oral antibiotics to manage chronic ear infections became less frequent.

In one test, the composition of Example 1 was used to treat a dog that had a history of chronic ear problems over approximately the previous six years. Throughout such six-year time period, several treatments, including various antibiotics and ear medications, had been used, to treat such ear infection. While such treatments all seemed to work for a period of time, none of such treatments was successful in completely eliminating the infection. However, when the composition of Example 1 above was administered, at a dosage of about 1 to 2 drops, in each ear, twice a day, for 10 days, a noticeable improvement of the symptoms, including the dog's hearing, could be seen by 3-4 days into the treatment; at the end of such treatment, the dog's ear infection had completely cleared up.

In another case, an animal practitioner provided animal owners with the composition of Example 1 for use in treating animals who suffered from prolonged chronic ear infections. The animal practitioner instructed the animal owners to administer the drops at a dosage of 4-5 drops in each ear, twice daily, for a period of time ranging from 7 days to 6 weeks, depending upon the severity of the infections. The owners were further instructed to first clean each infected ear with a commercially available ear cleansing product called Oti-Calm™, manufactured by DVM Pharmaceuticals of Miami, Fla., prior to each administration of the present composition, and then to administer drops of the present composition into the infected ears and massage the drops into the ear, and allow the drops to remain in the infected ear. After examining the treated animals, it was found that use of the composition resulted in 100% success rate in significantly reducing the inflammatory process observed in the ear canals and appropriately controlling infection, although known medications used in the past on such animals had failed. Additionally, no adverse effects were noted.

Those skilled in the art will now appreciate that an improved composition has been described that effectively treats a variety of ear infections in animals, including bacterial infections, fungal infections, and yeast infections. When formulated as described above, the active ingredients are more reliably maintained in solution, allowing the composition to be administered in more consistent dosages without the need to be shaken vigorously before each use, and with improved antibacterial effect.

While the present invention has been described with respect to preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

We claim:

1. A method of preparing a composition for the treatment of ear infections in animals, said method comprising the steps of:
   a. combining the following components in a container, the container having an open end:
      i. an antifungal agent;
      ii. a steroidal anti-inflammatory agent;
      iii. an anhydrous organic acid;
      iv. liquid dehydrated alcohol;
      v. an antibiotic agent; and
      vi. liquid propylene glycol;
   b. covering the open end of the container after step a. and before step c.;
   c. heating the contents of the container while the container is covered; and
   d. following step c, cooling the heated contents of the container while the container is covered.

2. The method of claim 1 wherein the step of covering the open end of the container includes the step of applying an impervious plastic film over the open end of the container prior to said heating step.

3. The method of claim 1 further comprising the step of stirring the contents of the container during said step of heating the contents of the container.

4. The method of claim 3 further comprising the step of stirring the contents of the container during said step of cooling the contents of the container.

5. The method of claim 1 wherein said heating step is performed until the contents of the container has changed from an initial cloudy yellow color to a clear reddish purple color.

* * * * *